(12) United States Patent
Rathnakar Reddy et al.

(10) Patent No.: US 11,623,933 B2
(45) Date of Patent: Apr. 11, 2023

(54) PROCESS FOR THE PREPARATION OF SODIUM (2R,5S,13AR)-7,9-DIOXO-10-((2,4,6-TRIFLUOROBENZYL) CARBAMOYL)-2,3,4,5,7,9,13,13A-OCTAHYDRO-2,5-METHANOPYRIDO [1',2':4,5]PYRAZINO[2,1-B] [1,3] OXAZEPIN-8-OLATE AND ITS POLYMORPHIC FORM

(71) Applicant: Honour Lab Limited, Hyderabad (IN)

(72) Inventors: Kura Rathnakar Reddy, Hyderabad (IN); Kesireddy Subhash Chander Reddy, Hyderabad (IN); Guda Yadav Reddy, Hyderabad (IN)

(73) Assignee: Honour Lab Limited, Hyderabad (IN)

( * ) Notice: Subject to any disclaimer, the term of this patent is extended or adjusted under 35 U.S.C. 154(b) by 25 days.

(21) Appl. No.: 17/252,425

(22) PCT Filed: Jun. 26, 2019

(86) PCT No.: PCT/IB2019/055386
§ 371 (c)(1),
(2) Date: Dec. 15, 2020

(87) PCT Pub. No.: WO2020/003151
PCT Pub. Date: Jan. 2, 2020

(65) Prior Publication Data
US 2021/0363158 A1 Nov. 25, 2021

(30) Foreign Application Priority Data

Jun. 28, 2018 (IN) .............................. 201841024051
Aug. 16, 2018 (IN) .............................. 201841030689

(51) Int. Cl.
*C07D 498/18* (2006.01)
*A61P 31/18* (2006.01)

(52) U.S. Cl.
CPC ............ *C07D 498/18* (2013.01); *A61P 31/18* (2018.01); *C07B 2200/13* (2013.01)

(58) Field of Classification Search
CPC ..................... C07B 2200/13; C07D 498/18
See application file for complete search history.

(56) References Cited

FOREIGN PATENT DOCUMENTS

| WO | 2014100323 A1 | 6/2014 | |
|---|---|---|---|
| WO | 2015196116 A1 | 12/2015 | |
| WO | 2015196137 A1 | 12/2015 | |
| WO | WO-2015196137 A1 * | 12/2015 | ........... A61K 31/513 |

OTHER PUBLICATIONS

Bhattacharya et al. (Brittain, ed. Polymorphism in Pharmaceutical Solids, 2009, p. 334.*
Caira, "Crystalline Polymorphism of Organic Compounds", Topics in Current Chemistry, vol. 198, p. 164 (1998).
International Search Report for PCT/IB2019/055386, dated Nov. 15, 2019.

* cited by examiner

*Primary Examiner* — Susanna Moore
(74) *Attorney, Agent, or Firm* — Caesar Rivise, PC

(57) ABSTRACT

The present invention relates to process for the preparation of sodium (2R,5S,13aR)-7,9-dioxo-10-((2,4,6-trifluorobenzyl )carbamoyl)-2,3,4,5,7,9,13,13a-octahydro-2,5-methanopyrido [1',2':4,5] pyrazino[2,1-b] [1,3] oxazepin-8-olate of Formula-I and its polymorphic form thereof.

7 Claims, 4 Drawing Sheets

Formula I

PROCESS FOR THE PREPARATION OF SODIUM (2R,5S,13AR)-7,9-DIOXO-10-((2,4,6-TRIFLUOROBENZYL) CARBAMOYL)-2,3,4,5,7,9,13,13A-OCTAHYDRO-2,5-METHANOPYRIDO[1',2':4,5]PYRAZINO[2,1-B] [1,3] OXAZEPIN-8-OLATE AND ITS POLYMORPHIC FORM

CROSS-REFERENCE TO RELATED APPLICATIONS

This application is a U.S. National Phase Application of PCT/IB2019/055386, filed Jun. 26, 2019, which claims priority to IN201841024051, filed Jun. 28, 2018 and IN201841030689, filed Aug. 16, 2018, the contents of which applications are incorporated herein by reference in their entireties for all purposes.

FIELD OF THE INVENTION

The present invention relates to a process for the preparation of sodium (2R,5S,13aR)-7,9-dioxo-10-((2,4,6-trifluorobenzyl)carbamoyl)-2,3,4,5,7,9,13,13a-octahydro-2,5-methanopyrido [1',2':4,5]pyrazino[2,1-b] [1,3] oxazepin-8-olate and its polymorphic form thereof.

BACKGROUND OF THE INVENTION

The present invention relates to an improved process for the preparation of Sodium (2R,5S,13aR)-7,9-dioxo-10-((2,4,6-trifluorobenzyl) carbamoyl)-2,3,4,5,7,9,13,13a-octahydro-2,5-Methanopyrido[1',2':4,5]pyrazino[2,1-b][1,3] oxazepin-8-olate compound of formula-1, represented by the following structural Formula:

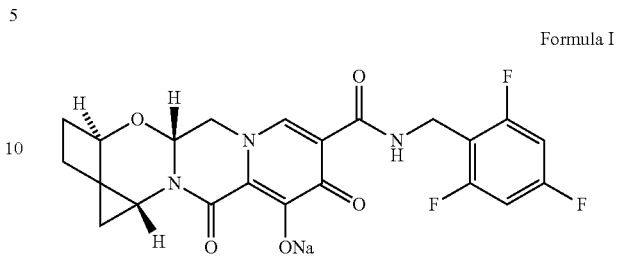

Formula I

Sodium(2R,5S,13aR)-7,9-dioxo-10-((2,4,6-trifluorobenzyl)carbamoyl)-2,3,4,5,7,9,13,13a-octahydro-2,5-Methanopyrido[1',2':4,5]pyrazino[2,1-b][1,3]oxazepin-8-olate is known to be Bictegravir sodium, which has been approved as the combination drug in US as Bictegravir; Emtricitabine; Tenofovir alafenamide under the trade name of BIKTARVY® for treating HIV.

(2R,5S,13aR)-7,9-dioxo-10-((2,4,6-trifluorobenzyl) carbamoyl)-2,3,4,5,7,9,13,13a-octahydro-2,5-Methanopyrido[1',2':4,5]pyrazino[2,1-b][1,3]oxazepin-8-olate (compound of formula-Ia), as well as its pharmaceutically acceptable salts are first known in U.S. Pat. No. 9,216,996 (US' 996).

US'996 has disclosed the following process for the preparation of (2R,5S,13aR)-7,9-dioxo-10-((2,4,6-trifluorobenzyl) carbamoyl)-2,3,4,5,7,9,13,13a-octahydro-2,5-methanopyrido[1',2':4,5]pyrazino[2,1-b][1,3] oxazepin-8-olate of Formula-Ia:

It has been observed that the above processes suffer from several drawbacks, such as HATU is used as condensing agent which gives the tetramethyl urea as a byproduct. It is very difficult to remove from the product. Using of HATU is inconvenient because of the price, which makes its use detrimental for industry. Further column chromatography has been used for isolation of compound of Formula Ia, which is difficult and cumbersome industrially.

U.S. Pat. No. 9,682,084 B2 (US'084) has disclosed the following process for the preparation of Form-III of (2R, 5S,13aR)-7,9-dioxo-10-((2,4,6-trifluorobenzyl) carbamoyl)-2,3,4,5,7,9,13,13a octahydro-2,5-Methanopyrido[1',2':4,5]pyrazino[2,1-b][1,3]oxazepin-8-olate:

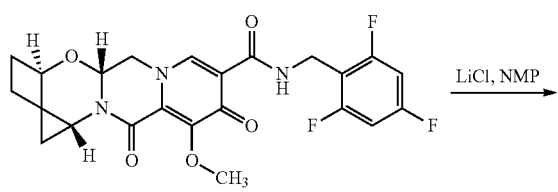

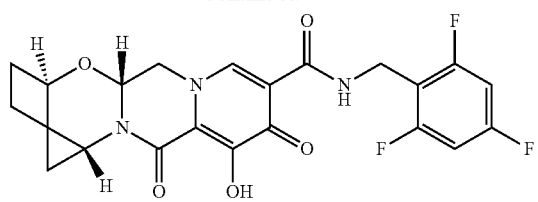

This patent disclosed LiCl and N-methyl-2-pyrrolidone for demethylation, however no disclosure about isolation of Lithiumsalt of (2R,5S,13aR)-7,9-dioxo-10-((2,4,6-trifluorobenzyl) carbamoyl)-2,3,4,5,7,9,13,13a octahydro-2,5-methanopyrido[1',2':4,5] pyrazino[2,1-b][1,3]oxazepin-8-olate.

US 201500368264 has disclosed the following process for the preparation of (2R,5S,13aR)-7,9-dioxo-10-((2,4,6-trifluorobenzyl)carbamoyl)-2,3,4,5,7,9,13,13a-octahydro-2,5-Methanopyrido[1',2':4,5]pyrazino[2,1-b][1,3]oxazepin-8-olate:

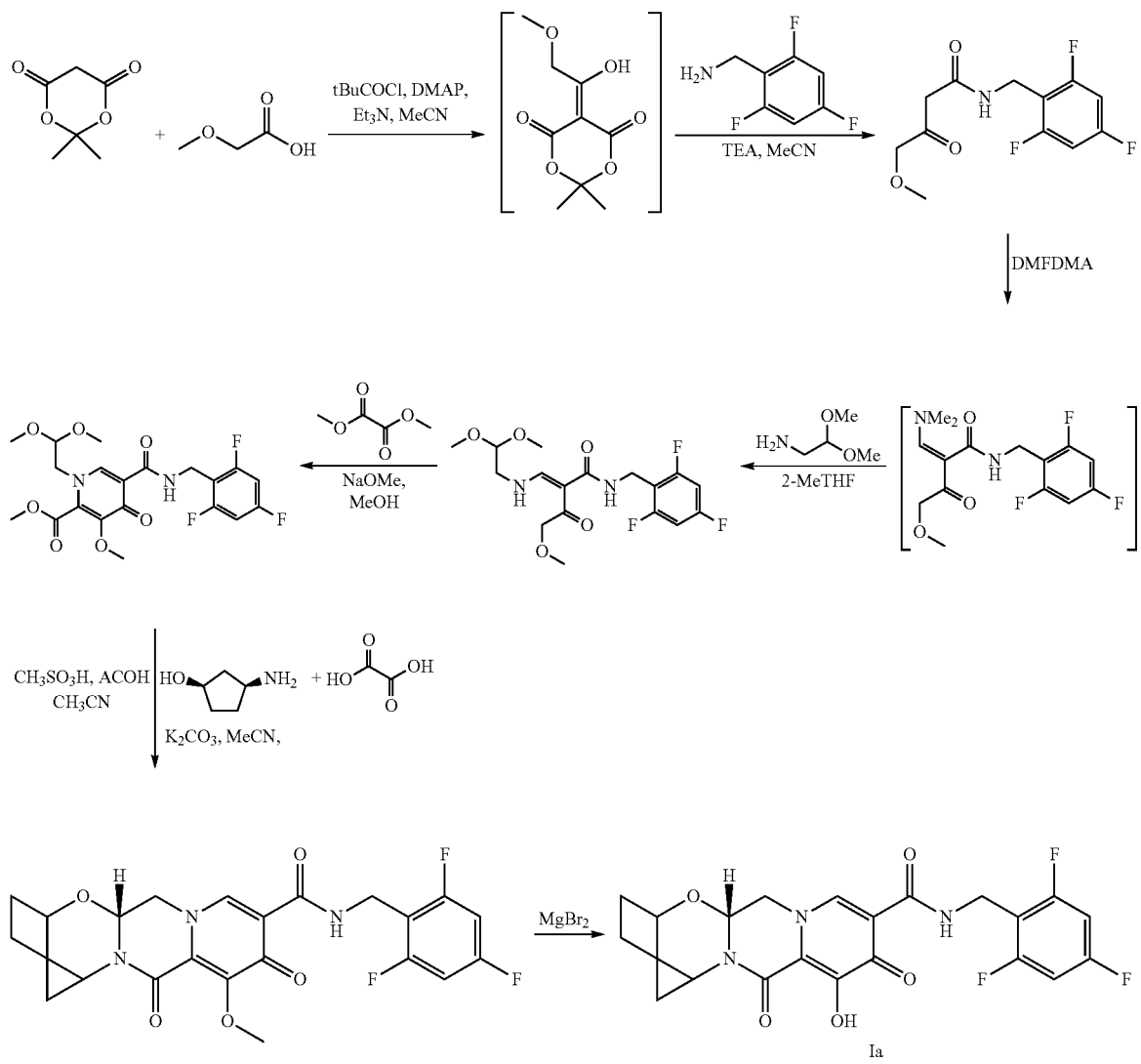

Further this patent discloses that "deprotection of methoxy group in presence of metal salt to obtain (2R,5S,13aR)-7,9-dioxo-10-((2,4,6-trifluorobenzyl)carbamoyl)-2,3,4,5,7,9,13,13a-octahydro-2,5-Methanopyrido[1',2':4,5]pyrazino[2,1-b][1,3] oxazepin-8-olate. The metal salt is selected from the group consisting of magnesium bromide, lithium chloride, lithium bromide and lithium iodide. In still further embodiments, the metal salt is lithium chloride".

These prior arts have used metal salts for demethylation and obtained crude product was purified by silica gel chromatography, which is cumbersome industrially. Further in any of the prior arts there is no disclosure about removal of impurities, which were formed during the prior-art process. Due to these impurities prior art process yielded sodium (2R,5S,13aR)-7,9-dioxo-10-((2,4,6-trifluorobenzyl)carbamoyl)-2,3,4,5,7,9,13,13a-octahydro-2,5-Methanopyrido [1',2':4,5]pyrazino[2,1-b][1,3] oxazepin-8-olate with low purity and yield. Hence, there is a need for an improved and commercially viable process for preparing compound of Formula-1, which is suitable industrially.

U.S. Pat. No. 9,708,342 B2 discloses Sodium (2R,5S,13aR)-7,9-dioxo-10-((2,4,6-trifluorobenzyl) carbamoyl)-2,3,4,5,7,9,13,13a-octahydro-2,5-Methanopyrido[1',2':4,5]pyrazino[2,1-b] [1,3] oxazepin-8-olate having X-ray powder diffraction peaks about 5.5, 16.1, 17.9, 19.5, 22.1, 22.5, 23.3, 28.5±0.2° 2θ, which is designated as Form-I, and provided single PXRD figure.

US'342 has disclosed the following process for the preparation of Sodium (2R,5S,13aR)-7,9-dioxo-10-((2,4,6-trifluorobenzyl) carbamoyl)-2,3,4,5,7,9,13,13a-octahydro-2,5-Methanopyrido[1',2':4,5]pyrazino[2,1-b][1,3] oxazepin-8-olate:

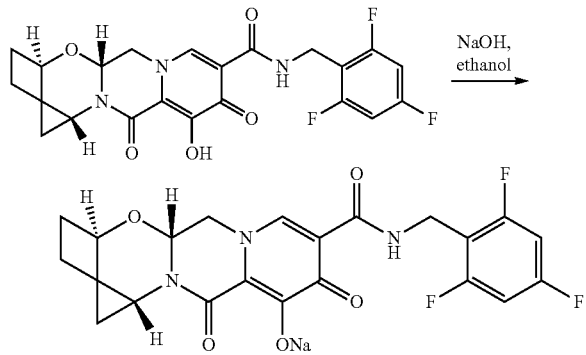

European medical agency (EMA) stated that, "Only one polymorphic form was identified during development of Sodium (2R,5S,13aR)-7,9-dioxo-10-((2,4,6-trifluorobenzyl) carbamoyl)-2,3,4,5,7,9,13,13a-octahydro-2,5-Methanopyrido[1',2':4,5]pyrazino[2,1-b] [1,3] oxazepin-8-olate." (Ref. EMA/293559/2018-Scientific discussion).

U.S. Pat. No. 9,682,084 B2 discloses the polymorphic forms of (2R,5S,13aR)-7,9-dioxo-10-((2,4,6-trifluorobenzyl) carbamoyl)-2,3,4,5,7,9,13,13a-octahydro-2,5-Methanopyrido[1',2':4,5] pyrazino[2,1-b] [1,3] oxazepin-8-olate free base designated as Crystalline Form I, Form II, Form III, Form IV, Form V, Form VI, Form VII and Form VIII and amorphous Form. Further this patent discloses the cocrystals (2R,5S,13aR)-7,9-dioxo-10-((2,4,6-trifluorobenzyl) carbamoyl)-2,3,4,5,7,9,13,13a-octahydro-2,5-Methanopyrido [1',2': 4,5]pyrazino [2,1-b] [1,3] oxazepin-8-olate, including Oxalic acid, Fumaric acid and Citric acid.

U.S. Pat. No. 9,682,084 B2 discloses the polymorphic forms of the (2R,5S,13aR)-7,9-dioxo-10-((2,4,6-trifluorobenzyl) carbamoyl)-2,3,4,5,7,9,13,13a-octahydro-2,5-Methanopyrido [1',2':4,5] pyrazino[2,1-b] [1,3] oxazepin-8-olate, potassium salt designated as Form-I, Form-II and Form-III.

During the development of the process the present inventors noticed that the Sodium (2R,5S,13aR)-7,9-dioxo-10-((2,4,6-trifluorobenzyl) carbamoyl)-2,3,4,5,7,9,13,13a-octahydro-2,5-Methanopyrido[1',2':4,5]pyrazino[2,1-b] [1,3] oxazepin-8-olate exhibits polymorphism and obtains new crystalline form, which is stable and PXRD 2θ values as well as figure is different from the known crystalline form of US'342.

OBJECTIVES OF THE INVENTION

The objective of the present invention, is to provide crystalline form of Sodium (2R,5S,13aR)-7,9-dioxo-10-((2,4,6-trifluorobenzyl)carbamoyl)-2,3,4,5,7,9,13,13a-octahydro-2,5-methanopyrido[1',2':4,5]pyrazino[2,1-b][1,3] oxazepin-8-olate.

Yet another objective of the present invention is to provide a process for the preparation of Crystalline Sodium (2R,5S,13aR)-7,9-dioxo-10-((2,4,6-trifluorobenzyl) carbamoyl)-2,3,4,5,7,9,13,13a-octahydro-2,5-Methanopyrido [1',2': 4,5]pyrazino[2,1-b][1,3] oxazepin-8-olate, which is consistent, reproducible, stable and industrially viable.

Another objective of the present invention is to prepare Sodium (2R,5S,13aR)-7,9-dioxo-10-((2,4,6-trifluorobenzyl) carbamoyl)-2,3,4,5,7,9,13,13a-octahydro-2,5-methanopyrido [1',2':4,5] pyrazino[2,1-b][1,3]oxazepin-8-olate having high purity and yield.

Another objective of the present invention is to provide a process for the preparation of Sodium (2R,5S,13aR)-7,9-dioxo-10-((2,4,6-trifluorobenzyl)carbamoyl)-2,3,4,5,7,9,13,13a-octahydro-2,5-Methanopyrido[1',2':4,5]pyrazino[2,1-b] [1,3]oxazepin-8-olate, which is economically and industrially feasible

SUMMARY OF THE INVENTION

The present invention relates to a Crystalline form of Sodium (2R,5S,13aR)-7,9-dioxo-10-((2,4,6-trifluorobenzyl) carbamoyl)-2,3,4,5,7,9,13,13a-octahydro-2,5-Methanopyrido [1',2':4,5]pyrazino[2,1-b][1,3] oxazepin-8-olate having the X-ray powder diffraction pattern shown in FIG. 1 and having 2θ peak of 9.0±0.2° 2θ; DSC is as shown in FIG. 2.

The present invention also relates to a process for the preparation of Sodium (2R,5S,13aR)-7,9-dioxo-10-((2,4,6-trifluorobenzyl) carbamoyl)-2,3,4,5,7,9,13,13a-octahydro-2,5-Methanopyrido[1',2':4,5] pyrazino [2,1-b][1,3] Oxazepin-8-olate crystalline HN-1 form, which comprises:

a) dissolving (2R,5S,13aR)-7,9-dioxo-10-((2,4,6-trifluorobenzyl)carbamoyl)-2,3,4,5,7,9,13,13a-octahydro-2,5-Methanopyrido[1',2':4,5]pyrazino[2,1-b][1,3] Oxazepin-8-olate, in an organic solvent, water and/or mixtures thereof;
b) optionally treatment with carbon;
c) preparing a source of sodium base;
d) adding step(c) to step-(a) or step-(a) to step(c);
e) heating the obtained reaction mixture to 40-50° C.;
f) cooling the obtained reaction mixture to room temperature; and
g) isolating Sodium (2R,5S,13aR)-7,9-dioxo-10-((2,4,6-trifluorobenzyl) carbamoyl)-2,3,4,5,7,9,13,13a-octahydro-2,5-Methanopyrido[1',2':4,5]pyrazino [2,1-b][1,3] oxazepin-8-olate in crystalline form.

In another aspect of the present invention, an improved process for preparing Sodium (2R,5S,13aR)-7,9-dioxo-10-((2,4,6-trifluorobenzyl)carbamoyl)-2,3,4,5,7,9,13,13a-octahydro-2,5-Methanopyrido[1',2':4,5]pyrazino[2,1-b][1,3] oxazepin-8-olate of compound Formula-I, Formula I

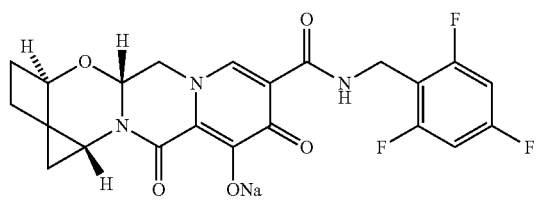

which comprises, a) reacting (2R,5S,13aR)-8-methoxy-7,9-dioxo-2,3,4,5,7,9,13,13a-octahydro-2,5-methano pyrido[1',2':4,5]pyrazino[2,1-b][1,3]oxazepin-10-carboxylic acid of Formula-III;

Formula III

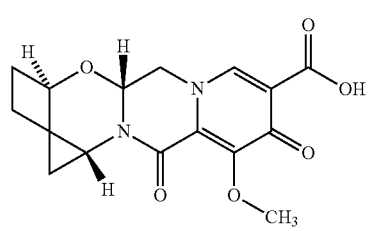

with compound of Formula-IV,

Formula V

wherein A represents Imidazole, Cl, Br or I; B represents Imidazole, —OR; R represents $C_{1-8}$ branched or straight chain alkyl group;

in presence of a suitable base and solvent to provide a compound of Formula V,

Formula V

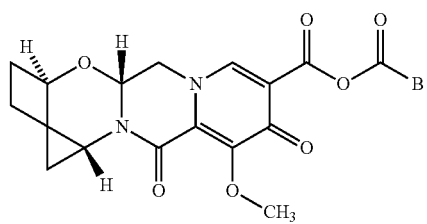

b) reacting compound of Formula-V with (2,4,6-trifluorophenyl) methanamine of Formula-VI;

Formula-VI

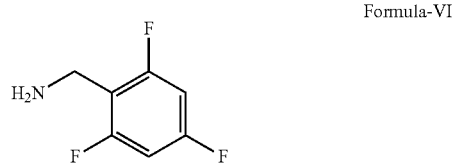 [SMILES: NCc1c(F)cc(F)cc1F]

to provide a compound of Formula VII,

Formula-VII

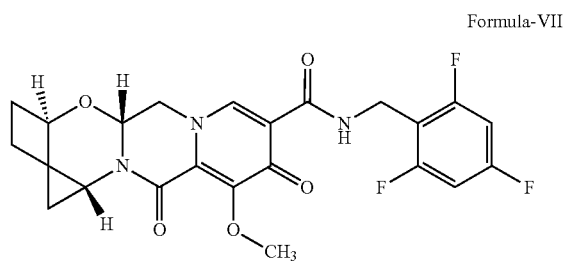 [SMILES: COc1c2n(cc(C(=O)NCc3c(F)cc(F)cc3F)c1=O)C[C@H]1O[C@@H]3CCC34C[C@H]4N1C2=O]

c) demethylating the compound of Formula-VII with lithium halide in a suitable solvent to provide compound of Formula II;

Formula-II

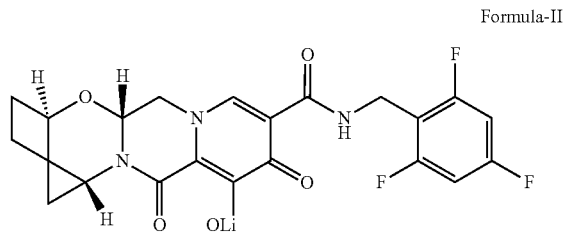

d) reacting the compound of Formula-II with an acid in presence of solvent to provide compound of Formula Ia;

Formula-Ia

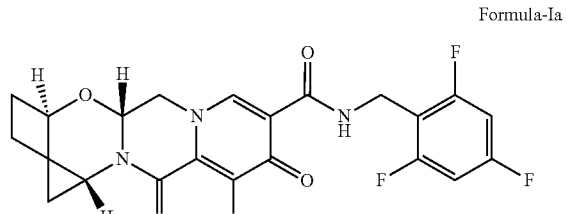

e) treating the compound of Formula Ia with sodium base in presence of suitable solvent to provide a compound of Formula I;

wherein compound of Formula-V may be optionally isolated or in situ reacted with compound of Formula VI.

In another aspect of the present invention, crystalline Form of Lithium (2R,5S,13aR)-7,9-dioxo-10-((2,4,6-trifluorobenzylcarbamoyl)-2,3,4,5,7,9,13,13a-octahydro-2,5-Methanopyrido[1',2':4,5]pyrazino[2,1-b][1,3] oxazepin-8-olate of Formula-II.

POWDER X-RAY DIFFRACTION METHOD

X-ray powder diffraction spectrum was measured on a broker axs D8 advance X-ray powder diffractometer having a copper-Kα radiation. Approximately 1 gm of sample was gently flattered on a sample holder and scanned from 2 to 50 degrees two-theta, at 0.02 degrees two theta per step and a step time of 10.8 seconds. The sample was simply placed on the sample holder. The sample was rotated at 30 rpm at a voltage 40 KV and current 35 mA.

Differential Scanning Calorimetry

Thermal properties of sodium (2R,5S,13aR)-7,9-dioxo-10-((2,4,6-trifluorobenzyl)carbamoyl)-2,3,4,5,7,9,13,13a-octahydro-2,5-methanopyrido[1',2': 4,5] pyrazino[2,1-b][1, 3]oxazepin-8-olate Form I and Form HN-1 were evaluated using a Differential Scanning calorimetry (DSC) instrument (TA Q2000, TA Instruments) Approximately 5 to 10 mg of solid sample was placed in a standard aluminum pan vented with a pinhole for each experiment and heated at a rate of 10° C./min under a 50 mL/min nitrogen purge.

DETAILED DESCRIPTION OF THE INVENTION

Figure 1:
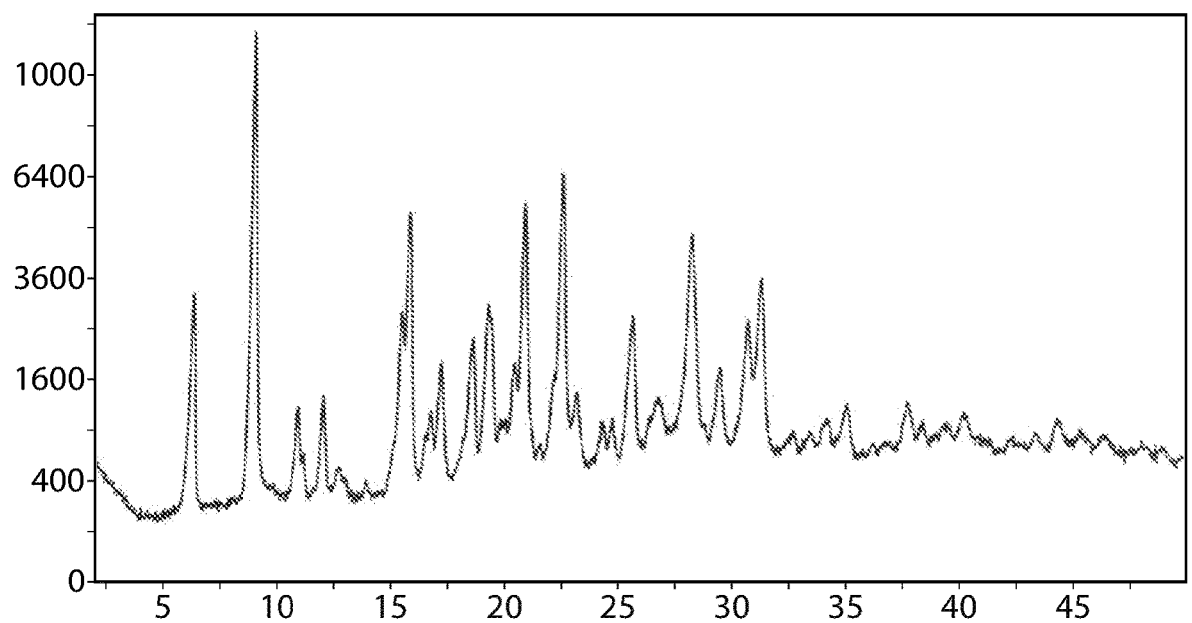
FIG. 1. is a a X-ray powder diffraction spectrum of crystalline Form HN-1 Sodium (2R,5S,13aR)-7,9-dioxo-10-((2,4,6-trifluorobenzyl) carbamoyl)-2,3,4,5,7,9,13,13a-octahydro-2,5-Methanopyrido[1',2': 4,5]pyrazino [2,1-b][1,3] oxazepin-8-olate.
Figure 2:
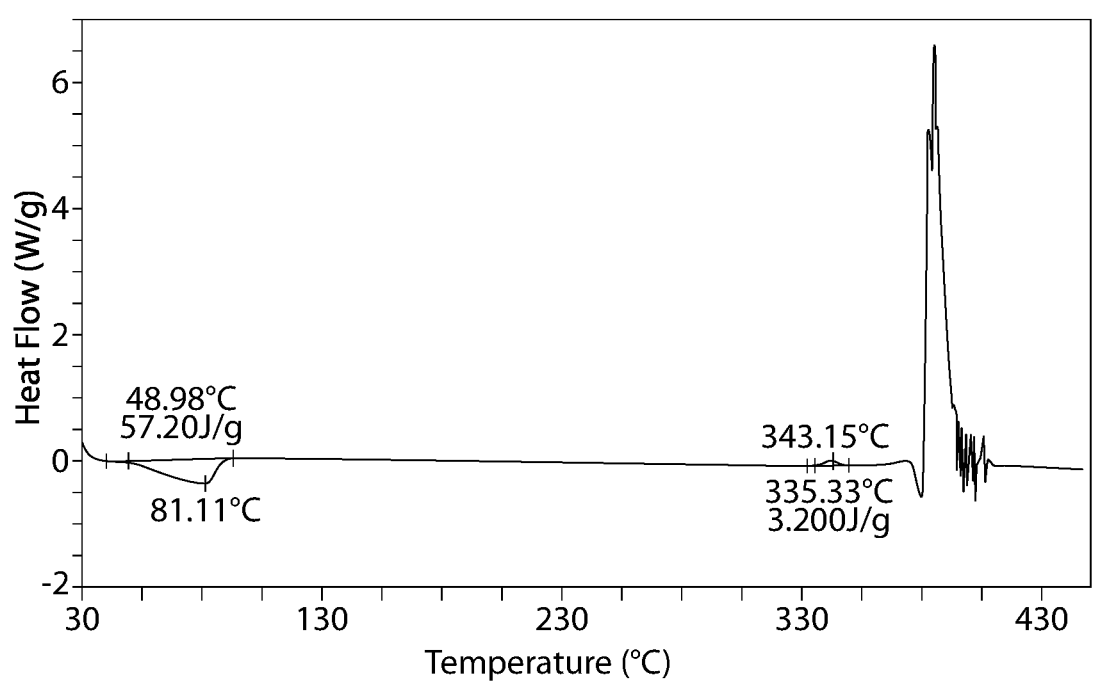
FIG. 2. is a DSC of crystalline Form HN-1 Sodium (2R,5S,13aR)-7,9-dioxo-10-((2,4,6-Trifluorobenzyl)carbamoyl)-2,3,4,5,7,9,13,13a-octahydro-2,5-Methanopyrido [1',2':4,5] pyrazino [2,1-b][1,3] oxazepin-8-olate.
Figure 3:
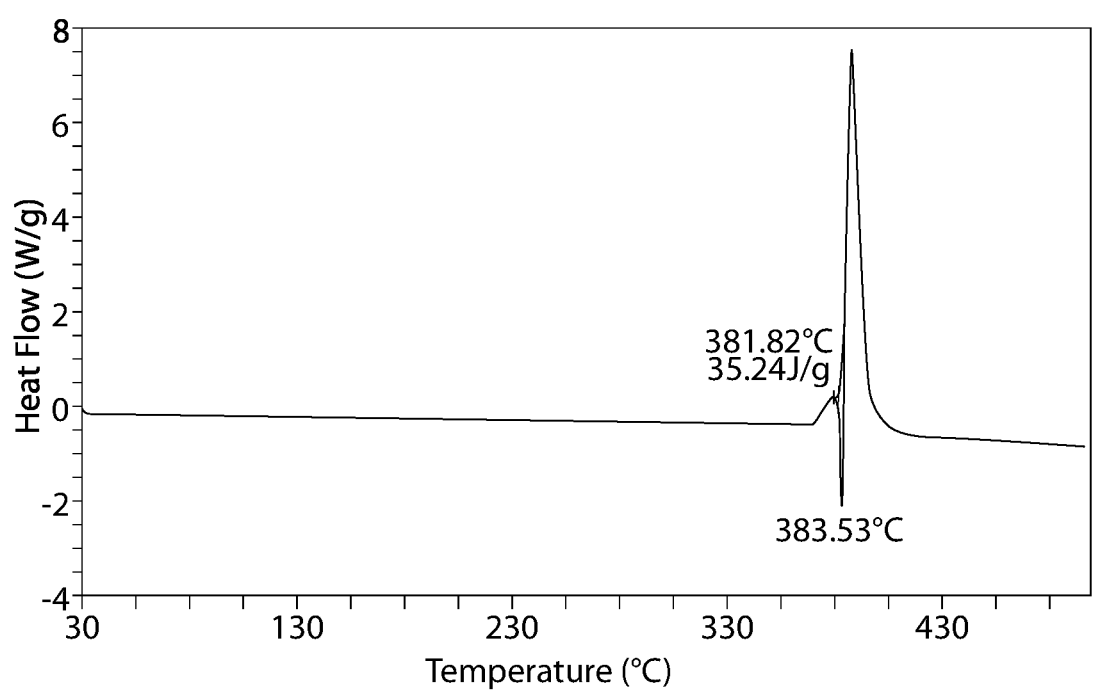
FIG. 3. is a DSC of Form-I of Sodium (2R,5S,13aR)-7,9-dioxo-10-((2,4,6-Trifluorobenzyl)carbamoyl)-2,3,4,5,7,9, 13,13a-octahydro-2,5-Methanopyrido[1',2':4,5] pyrazino [2,1-b][1,3] oxazepin-8-olate.

The present invention relates to a Crystalline form of Sodium (2R,5S,13aR)-7,9-dioxo-10-((2,4,6-trifluorobenzyl) carbamoyl)-2,3,4,5,7,9,13,13a-octahydro-2,5-Methanopyrido [1',2':4,5]pyrazino[2,1-b][1,3] oxazepin-8-olate having the X-ray powder diffraction pattern shown in FIG. 1 and having 2θ peak of 9.0±0.2° 2θ; DSC is as shown in FIG. 2.

In another embodiment of the present invention, Sodium (2R,5S,13aR)-7,9-dioxo-10-((2,4,6-trifluorobenzyl)carbamoyl)-2,3,4,5,7,9,13,13a-octahydro-2,5-Methanopyrido [1',2':4,5]pyrazino[2,1-b][1,3] oxazepin-8-olate HN-1 crystalline form with water content approximately ranging from 3 to 6% w/w. This form is characterized by a DSC thermogram as reported in FIG. 2, with two exothermic peaks at ~81° C. and ~383° C.; and powder X-ray diffraction spectrum as illustrated in FIG. 1, wherein the most intense diffraction peaks fall at 6.4, 9.0, 12.0, 15.9, 17.2, 19.4, 20.9, 22.6, 23.2 and 25.7±0.2° in 2θ.

In another embodiment of the present invention, isolated crystalline form of Sodium (2R,5S,13aR)-7,9-dioxo-10-((2, 4,6-trifluorobenzyl)carbamoyl)-2,3,4,5,7,9,13,13a-octahydro-2,5-Methanopyrido [1',2':4,5]pyrazino[2,1-b][1,3] oxazepin-8-olate has water content in the range of 3-6% w/w by Karl Fischer method.

In another embodiment of the present invention, isolated crystalline form of Sodium (2R,5 S,13 aR)-7,9-dioxo-10-((2,4,6-trifluorobenzyl)carbamoyl)-2,3,4,5,7,9, 13,13a-octahydro-2,5-Methanopyrido [1',2':4,5]pyrazino[2,1-b][1,3] oxazepin-8-olate has been designated as Form HN-1.

In another embodiment of the present invention, a process for the preparation crystalline HN-form of Sodium (2R,5 S,13 aR)-7,9-dioxo-10-((2,4,6-trifluorobenzypcarbamoyl)-2,3,4,5,7,9,13,13a-octahydro-2,5-Methanopyrido [1',2':4,5] pyrazino[2,1-b][1,3]oxazepin-8-olate, which comprises dissolving (2R,5S,13aR)-7,9-dioxo-10-((2,4,6-trifluorobenzyl) carbamoyl)-2,3,4,5,7,9,13,13a-octahydro-2,5-Methanopyrido[1',2':4,5]pyrazino[2,1-b] [1,3]oxazepin-8-olate in in an organic solvent, water or mixture thereof; optionally treating with carbon; preparing a source of sodium base and added to the obtained reaction mixture (or) reaction mixture added to a source of sodium base slowly followed by heating the obtained reaction mixture to 40-50° C. Cooling the obtained reaction mixture to room temperature and isolating crystalline HN-1 form of Sodium(2R,5S,13aR)-7,9-dioxo-10-((2,4,6-trifluorobenzyl)carbamoyl)-2,3,4,5,7,9,13,13a-octahydro-2,5-methanopyrido [1',2':4,5] pyrazino [2,1-b][1, 3] oxazepin-8-olate.

In another embodiment of the present invention, a process for the preparation Sodium (2R,5S,13aR)-7,9-dioxo-10-((2, 4,6-trifluorobenzyl) carbamoyl)-2,3,4,5,7,9,13,13a-octahydro-2,5-methanopyrido [1',2':4,5]pyrazino[2,1-b][1,3] oxazepin-8-olate, which comprises dissolving (2R,5S, 13aR)-7,9-dioxo-10-((2,4,6-trifluorobenzyl) carbamoyl)-2, 3,4,5,7,9,13,13a-octahydro-2,5-methanopyrido [1',2':4,5] pyrazino[2,1-b][1,3]oxazepin-8-olate in an organic solvent, water or mixture thereof; wherein the obtained reaction mixture treated with carbon and removed the carbon through hyflow. wherein organic solvent is selected from the groups comprising of halogenated solvents, alcohols, ketonic solvents, ethers, esters, hydrocarbons, nitriles, dimethylformamide, dimethylsulfoxide, and dimethylacetamide at room temperature; wherein the halogenated solvents are selected from the group comprising of dichloromethane (MDC), ethylene dichloride (EDC), chloroform and the like; alcohols are selected from the group comprising of methanol, ethanol, isopropanol, 1-butanol, 2-butanol, 2-methyl-2-propanol, 1-pentanol, 2,3 pentanol, 2-methyl-2-butanol, 2-methyl-1-butanol, 3-methyl-2-butanol, and the like; ketonic solvents are selected from the group comprising of acetone, methylethyl ketone, methyl isobutyl ketone and the like; ethers are selected from the group comprising of tetrahydrofuran (THF), 2-methyltetrahydrofuran (MeTHF), diethyl ether, isopropyl ether, methyl isobutylether, methyl t-Bu ether (MTBE), dioxane and the like; esters are selected from the group comprising of ethyl acetate, isopropyl acetate and the like; hydrocarbons are selected from the group comprising of toluene, heptane, hexane, cyclohexane xylene and the like; nitriles are selected from the group comprising of acetonitrile, propionitrile, butyronitrile, acrylonitrile.

In another embodiment of the present the invention, For preparing crystalline Form HN-1 of Formula-I, wherein source of sodium base is prepared by dissolving sodium base in water.

In another embodiment throughout the invention, wherein sodium base is selected from the group comprising of Sodium hydroxide, sodium alkoxide, sodium-2-ethylhexanoate, sodium acetate, sodium bicarbonate, sodium carbonate, sodium lactate, sodium dihydrogen phosphate; wherein sodium base is added to the obtained reaction mixture (or) reaction mixture is added to a source of sodium base slowly over a period of 1 hour at room temperature.

In another embodiment throughout the invention, heating the obtained reaction mixture for 1 hour, wherein heating temperature is 40-60° C., preferably 45°±5° C. and there after cooled 25-30° C.

In another embodiment throughout the invention, the mixture of solvents means two or more solvents and room temperature is considered as 25-30° C.

The another embodiment throughout the invention, the isolation of crystalline Sodium (2R,5S,13aR)-7,9-dioxo-10-((2,4,6-trifluorobenzyl)carbamoyl)-2,3,4,5,7,9,13,13a-octahydro-2,5-Methanopyrido[1',2':4,5]pyrazino [2,1-b][1,3]oxazepin-8-olate is carried out by way of cooling, anti solvent technique, evaporation of solvent and filtration techniques.

In another embodiment throughout the invention, (2R,5S,13aR)-7,9-dioxo-10-((2,4,6-trifluorobenzyl) carbamoyl)-2,3,4,5,7,9,13,13a-octahydro-2,5-Methanopyrido[1',2':4,5]pyrazino[2,1-b][1,3]oxazepin-8-olate is either crystalline or amorphous.

The present inventors have also studied the stability of crystalline Form HN-1 at 40° C. and 75% RH for 6 months and found that the product complies with the initial results and found to be stable.

The stability of sample was tested by storing the samples at 40° C./75% relative humidity (RH) and 25° C./60% RH for 6 months. The stability of samples was tested by PXRD, HPLC and water content was measured by Karl Fischer method.

Data collected during these tests at 25° C./60% RH and 40° C./75% RH are as shown below:

| Time point | Storage Conditions | Physical form (as assessed by PXRD) | Water content by Karl Fischer method | Purity by HPLC |
| --- | --- | --- | --- | --- |
| Initial | | Crystalline Form HN-1 | 4.2 | 99.82% |
| 4 month | 25° C./60% RH | Crystalline Form HN-1 | 3.7 | 99.78% |
| | 40° C./75% RH | Crystalline Form HN-1 | 3.6 | 99.78% |
| 5 month | 25° C./60% RH | Crystalline Form HN-1 | 3.9 | 99.78% |
| | 40° C./75% RH | Crystalline Form HN-1 | 3.9 | 99.77% |
| 6 month | 25° C./60% RH | Crystalline Form HN-1 | 3.8 | 99.78% |
| | 40° C./75% RH | Crystalline Form HN-1 | 3.8 | 99.78% |

The stability test revealed no changed in PXRD pattern and also in water content. There is no significant decrease in purity after storage, indicating that crystalline Form HN-1 of Sodium(2R,5S,13aR)-7,9-dioxo-10-((2,4,6-trifluorobenzyl) carbamoyl)-2,3,4,5,7,9,13,13a-octahydro-2,5-Methanopyrido [1',2':4,5]pyrazino[2,1-b][1,3] oxazepin-8-olate, (Form HN-1) is physically and chemically stable at 25° C./60% RH and 40° C./75% RH conditions.

In another embodiment of the present invention provides an improved process for the preparation of Sodium (2R,5S,13aR)-7,9-dioxo-10-((2,4,6-trifluorobenzyl)carbamoyl)-2,3,4,5,7,9,13,13a-octahydro-2,5-Methanopyrido[1',2':4,5] pyrazino[2,1-b][1,3] oxazepin-8-olate of compound formula-I, which comprises: reacting (2R,5S,13aR)-8-methoxy-7,9-dioxo-2,3,4,5,7,9,13,13a-octahydro-2,5-methanopyrido[1',2':4,5]pyrazino[2,1-b][1,3] oxazepin-10-carboxylic acid of Formula-III with compound of Formula-IV in presence of suitable base and solvent to provide a compound of Formula-V, wherein compound of Formula-V is optionally isolated or in situ reacting with (2,4,6-trifluorophenyl) methanamine compound of Formula VI to provide a compound of Formula VII. Demethylating the compound of Formula-VII with lithium halide in a suitable solvent to provide compound of Formula II. Further compound of Formula-II subjected to an acid in presence of solvent to provide compound of Formula Ia. Compound of Formula Ia is reacted with sodium base to provide compound of Formula I.

In another embodiment of the present invention, reacting (2R,5S,13aR)-8-methoxy-7,9-dioxo-2,3,4,5,7,9,13,13a-octahydro-2,5-methanopyrido[1',2':4,5]pyrazino[2,1-b][1,3] oxazepin-10-carboxylic acid of Formula-III with compound of Formula-IV in presence of suitable base and solvent at a temperature in the range of 0° C. to −15° C. to provide a compound of Formula-V.

In another embodiment of the present invention, wherein the compound of Formula-IV represented as

Formula-IV wherein A represents Imidazole, Cl, Br or I; B represents Imidazole, —OR; R represents $C_{1-8}$ branched or straight chain alkyl group has been used.

In another embodiment of the present invention, suitable base is selected from the group comprising of organic or inorganic base; inorganic base is selected from the group comprising of "alkali metal hydroxides" such as lithium hydroxide, sodium hydroxide, potassium hydroxide and the tike; "alkali metal carbonates" such as sodium carbonate, potassium carbonate, lithium carbonate and the like; "alkali metal bicarbonates" such as sodium bicarbonate, potassium bicarbonate, lithium bicarbonate and the like; "alkali metal hydrides" such as potassium hydride, lithium hydride and the like; "alkali metal alkoxides" such as sodium methoxide, sodium ethoxide, sodium tert-butoxide, potassium methoxide, potassium ethoxide, potassium tert-butoxide and ammonia; organic base is selected from the group comprising of triethyl amine, methyl amine, ethyl amine, tribenzylamine, isopropyl amine, diisopropyl amine, diisopropylethylamine, N-methylmorpholine, N-ethylmorpholine, piperidine, dimethyl aminopyridine, morpholine, pyridine, 2,6-lutidine or mixtures thereof;

In another embodiment of the present invention, wherein compound of Formula-V is optionally isolated or in situ reacting with (2,4,6-trifluorophenyl) methanamine compound of Formula VI to provide a compound of Formula VII, which is further crystallizing in a suitable solvent or mixtures thereof; wherein suitable solvent for condensation of compound of Formula-III with compound of Formula-IV and crystallization solvent for compound Formula-VII is selected from the group comprising of "hydrocarbon solvents" such as n-hexane, n-heptane, cyclohexane, toluene, pentane, cycloheptane, methylcyclohexane, xylene; "chloro solvents" such as dichloromethane, dichloroethane, chloroform, carbon tetrachloride; "alcoholic solvents" such as methanol, ethanol, n-propanol, isopropanol, n-butanol, isobutanol, t-butanol, 2-nitroethanol, ethylene glycol, propylene glycol, 2-methoxyethanol, 1,2-ethoxyethanol, pentanol, neo-pentyl alcohol, t-pentyl alcohol or mixture thereof.

In another embodiment of the present invention, demethylating the compound of formula-VII with lithium halide in a suitable solvent to provide compound of Formula II; wherein suitable solvents for demethylation step is selected from the group comprising of "nitrile solvents" such as acetonitrile, propionitrile, isobutyronitrile or mixture thereof; lithium halides can be lithium chloride, lithium bromide and lithium iodide. Preferably Lithium bromide. Lithium halide has been added in one lot or lot wise in 2 or 3 portions. Where in demethylation reaction proceeds at about 50° C. to about 70° C. for period of 2-5 hours; preferably 60-65° C. for a period of 2-3 hours.

In another embodiment of the present invention, Lithium (2R,5S,13aR)-7,9-dioxo-10-((2,4,6-trifluorobenzylcarbamoyl)-2,3,4,5,7,9,13,13a-octahydro-2,5-methanopyrido[1',2':4,5] pyrazino[2,1-b][1,3]oxazepin-8-olate of Formula-II has been isolated in crystalline form.

In another embodiment of the present invention, compound of Formula-II reacted with an acid in presence of suitable solvent to provide compound of Formula Ia and optionally purifying the compound of Formula-Ia with a suitable solvent. where in acid is selected from the group comprising of hydrochloric acid, aqueous hydrochloric acid, methanolic-HCl, ethanolic-HCl, IPA-HCl, hydrochloric acid gas, sulphuric acid and acetic acid; where insuitable solvent for acidification and purification for compound of Formula-Ia is selected from the group comprising of "alcoholic presence of suitable solvent to provide compound of Formula I. wherein sodium base is defined above.

In another embodiment of the present invention, wherein Sodium base solution is prepared by dissolving sodium hydroxide in a suitable solvent slowly in a period of 1 hour at 25-30° C.; wherein suitable solvent is selected from the group comprising of chloro solvents, alcoholic solvents. chloro solvents such as such as dichloromethane, dichloroethane, chloroform, carbon tetrachloride; alcoholic solvents such as methanol, ethanol, n-propanol, isopropanol, n-butanol, isobutanol, t-butanol, ethylene glycol, propylene glycol, 2-methoxyethanol, 1,2-ethoxyethanol, diethylene glycol, pentanol, neo-pentyl alcohol, t-pentyl alcohol, cyclohexanol, benzyl alcohol, water or mixtures thereof;

In another embodiment of the present invention, the present inventors have repeated the prior art process and observed the several impurities and needed the number of purifications to obtain the sodium (2R,5S,13aR)-7,9-dioxo-10-((2,4,6-trifluorobenzylcarbamoyl)-2,3,4,5,7,9,13,13a-octahydro-2,5-methanopyrido[1',2':4,5] pyrazino[2,1-b][1,3] oxazepin-8-olate compound of Formula I as per ICH limits. Due to Purifications of compound of Formula I, yield has been getting low.

As per the comparison, it is to be noted that as per the current patent application process the impurities, which were not controlled in prior art process, were controlled with in the ICH limits i.e <0.15%, and doing so the compound of Formula I obtained with high yield and high purity as well as avoids the use of column chromatography which is cumbersome industrially.

| S. No | Impurity structure | Name of the Impurity | Prior art process by (by HPLC) | Present invention process (by HPLC) |
|---|---|---|---|---|
| 1. | Impurity-A | Diastereomer impurity | ~3% | <0.15% |
| 2. | Impurity-B | Hydroxy analog impurity | ~2% | <0.15% | solvents" such as methanol, ethanol, n-propanol, isopropanol, n-butanol, isobutanol, t-butanol, ethylene glycol, propylene glycol, 2-methoxyethanol, 1,2-ethoxyethanol, diethylene glycol, pentanol, neo-pentyl alcohol, t-pentyl alcohol, cyclohexanol, benzyl alcohol; "polar solvents" such as water or mixtures thereof. Purification of compound of Formula-Ia is carried out at temperature ranging from 50° C. to 70° C., preferably at 60-65° C., for a period of 1-2 hours.

In another embodiment of the present invention, where in the compound of Formula Ia reacted with a sodium base in The present invention involves the isolation of lithium salt (2R,5S,13aR)-7,9-dioxo-10-((2,4,6-trifluorobenzylcarbamoyl)-2,3,4,5,7,9,13,13a-octahydro-2,5-methanopyrido [1',2':4,5] pyrazino[2,1-b][1,3] oxazepin-8-olate, which makes the process easy industrially and achieve the ICH limits of the impurities.

The invention of the present application will be explained in more detail with reference to the following examples, which should not be construed as limiting the scope of the invention in any manner.

EXAMPLES

Example-1: Preparation of Crystalline Sodium (2R, 5S,13aR)-7,9-dioxo-10-((2,4,6-trifluorobenzyl)carbamoyl)-2,3,4,5,7,9,13,13a-octahydro-2,5-Methanopyrido [1',2':4,5]pyrazino[2,1-b][1,3]oxazepin-8-olate Dissolving (2R,5S,13aR)-7,9-dioxo-10-((2,4,6-trifluorobenzyl)carbamoyl)-2,3,4,5,7,9,13, 13a-octahydro-2,5-Methanopyrido[1',2':4,5]pyrazino [2,1-b][1,3] oxazepin-8-olate (100 gm) in a mixture of MDC and Methanol (350 ml: 650 ml) at room temperature. Carbon (2 gm) has been added to the reaction mixture and stirred for 10-15 minutes. The carbon has been removed through hyflow. Washing hyflow bed with mixture of MDC and Methanol (50 ml: 100 ml). To the obtained filtrate aq NaOH (10 gm NaOH in 50 ml water) was added slowly for 30-45 minutes at room temperature and the reaction mixture heated to 40-45° C. and stirred 1 hour. Thereafter reaction mixture cooled to room temperature and stirred for 1 hour. The obtained solid was filtered and washed with Methanol (50 ml) followed by drying at 45-50° C. to yield crystalline Sodium (2R,5S,13aR)-7,9-dioxo-10-((2,4,6-trifluorobenzyl) carbamoyl)-2,3,4,5,7,9,13,13a-octahydro-2,5-Methanopyrido [1',2':4,5]pyrazino[2,1-b][1,3]oxazepin-8-olate. pxrd pattern shown in FIG. 1.

Yield: 100 gm; Purity by HPLC (by chromatography): 99.82%

Example-2: Preparation of Crystalline Sodium (2R, 5S,13aR)-7,9-dioxo-10-((2,4,6-trifluorobenzyl)carbamoyl)-2,3,4,5,7,9,13,13a-octahydro-2,5-Methanopyrido [1',2':4,5] Pyrazino[2,1-b][1,3]oxazepin-8-olate (2R,5S,13aR)-7,9-dioxo-10-((2,4,6-trifluorobenzyl)carbamoyl)-2,3,4,5,7,9,13, 13a-octahydro-2,5-Methanopyrido [1',2':4,5]pyrazino[2,1-b][1,3]oxazepin-8-olate (10 gm) was dissolved in a mixture of MDC and Methanol (35 ml: 65 ml) at room temperature. Carbon (0.2 gm) was added to the reaction mixture and stirred for 10-15 minutes. The carbon removed through hyflow. To the obtained filtrate aq $Na_2CO_3$ (2.4 gm $Na_2CO_3$ in 5 ml water) was added slowly at room temperature and the reaction mixture heated to 40-45° C. and stirred 1 hour. Thereafter reaction mixture cooled to room temperature and stirred for 1 hour. The obtained solid was filtered and washed with Methanol (50 ml) followed by drying at 45-50° C. to afford the title compound in ~95% yield as depicted in FIG. 1.

Purity by HPLC (by chromatography):99.78%

Example-3: Preparation of Crystalline Sodium (2R, 5S,13aR)-7,9-dioxo-10-((2,4,6-trifluorobenzyl)carbamoyl)-2,3,4,5,7,9,13,13a-octahydro-2,5-Methanopyrido [1',2':4,5] Pyrazino[2,1-b][1,3]oxazepin-8-olate (2R,5S,13aR)-7,9-dioxo-10-((2,4,6-trifluorobenzyl)carbamoyl)-2,3,4,5,7,9,13, 13a-octahydro-2,5-Methanopyrido [1',2':4,5]pyrazino[2,1-b][1,3]oxazepin-8-olate (10 gm) was dissolved in a mixture of MDC and Isopropyl alcohol (IPA) (35 ml: 65 ml) at room temperature. Carbon (0.2 gm) was added to the reaction mixture and stirred for 10-15 minutes. The carbon removed through hyflow. To the obtained filtrate aq NaOH (1 gm NaOH in 5 ml water) was added slowly at room temperature and the reaction mixture heated to 40-45° C. and stirred 1 hour. Thereafter reaction mixture cooled to room temperature and stirred for 1 hour. The obtained solid was filtered and washed with IPA followed by drying at 45-50° C. to afford the title compound in ~95% yield as depicted in FIG. 1.

Purity by HPLC (by chromatography):99.7%

Example-4: Preparation of Crystalline Sodium (2R, 5S,13aR)-7,9-dioxo-10-((2,4,6-trifluorobenzyl)carbamoyl)-2,3,4,5,7,9,13,13a-octahydro-2,5-Methanopyrido [1',2':4,5] Pyrazino[2,1-b][1,3]oxazepin-8-olate (2R,5S,13aR)-7,9-dioxo-10-((2,4,6-trifluorobenzyl)carbamoyl)-2,3,4,5,7,9,13, 13a-octahydro-2,5-Methanopyrido [1',2':4,5]pyrazino[2,1-b][1,3]oxazepin-8-olate (10 gm) was dissolved in a mixture of MDC and Acetone (35 ml: 65 ml) at room temperature. Carbon (0.2 gm) was added to the reaction mixture and stirred for 10-15 minutes. The carbon removed through hyflow. To the obtained filtrate aq NaOH (1 gm NaOH in 5 ml water) was added slowly at room temperature and the reaction mixture heated to 40-45° C. and stirred 1 hour. Thereafter reaction mixture cooled to room temperature and stirred for 1 hour. The obtained solid was filtered and washed with acetone followed by drying at 45-50° C. to afford the title compound in ~95% yield as depicted in FIG. 1.

Purity by HPLC (by chromatography):99.81%

Example-5: Preparation of Crystalline Sodium (2R, 5S,13aR)-7,9-dioxo-10-((2,4,6-trifluorobenzyl)carbamoyl)-2,3,4,5,7,9,13,13a-octahydro-2,5-Methanopyrido [1',2':4,5] Pyrazino[2,1-b][1,3]oxazepin-8-olate (2R,5S,13aR)-7,9-dioxo-10-((2,4,6-trifluorobenzyl)carbamoyl)-2,3,4,5,7,9,13, 13a-octahydro-2,5-Methanopyrido [1',2': 4,5]pyrazino[2,1-b][1,3]oxazepin-8-olate (10 gm) was dissolved in a mixture of MDC and Methanol (35 ml: 65 ml) at room temperature. Carbon (0.2 gm) was added to the reaction mixture and stirred for 10-15 minutes. The carbon removed through hyflow. Charged aq NaOH (1 gm NaOH in 5 ml water) in an another RB flask and added above filtrate slowly at room temperature and the reaction mixture heated to 40-45° C. and stirred 1 hour. Thereafter reaction mixture cooled to room temperature and stirred for 1 hour. The obtained solid was filtered and washed with methanol followed by drying at 45-50° C. to afford the title compound in ~95% yield as depicted in FIG. 1.

Purity by HPLC (by chromatography):99.69%

Example-6: Preparation of (2R,5S,13aR)-8-methoxy-7,9-dioxo-N-[(2,4,6-trifluorophenyl) methyl]-2,3,4,5,7,9,13,13a-octahydro-2,5-methanopyrido [1',2':4,5]pyrazino[2,1-b][1,3] oxazepine-10-carboxamide (Compound of Formula-VH)

Charged (2R,5S,13aR)-8-methoxy-7,9-dioxo-2,3,4,5,7,9, 13,13a-octahydro-2,5-methano pyrido[1',2':4,5]pyrazino[2, 1-b][1,3]oxazepine-10-carboxylicacid, (60 gm, 0.1874 moles) in methylene chloride (390 ml) at 25-30° C. under nitrogen. Cooled the reaction mixture to −15 to −10° C. N-methylmorpholine (20.7 gm, 0.2047 moles) was added to the reaction mixture at −15 to −10° C. Isobutylchloroformate (28 gm, 0.205 moles) in methylene chloride (60 ml) was added for 1 hr to the cold reaction mass. (2,4,6-trifluorophenyl) methanamine (33 gm, 0.204 moles) in methylene chloride (60 ml) was added to the above reaction mixture for 45 minutes at −20 to −15° C. Raised the temperature to 25-30° C. and stirred for 2.30 hrs. After completion of reaction, the reaction mass was washed with sodiumbicarbonate (120 ml), 1N HCl (120 ml) water (120 ml) and concentrated. The Concentrated mass diluted with IPA (60 ml) and stirred for 20 minutes. n-heptane was added to the reaction mass for 30 minutes at 25-30° C. and stirred for 3 hours to crystallize the product. The product was filtered and dried to yield the title compound.

Yield-90%; Purity by HPLC (by chromatography): 94.16%.

Example-7: Preparation of Lithium (2R,5S,13aR)-7, 9-dioxo-10-((2,4,6-trifluorobenzyl) carbamoyl)-2,3, 4,5,7,9,13,13a-octahydro-2,5-methanopyrido[1',2':4, 5]pyrazino[2,1-b] [1,3] oxazepin-8-olate (Compound of Formula-II)

Figure 4:
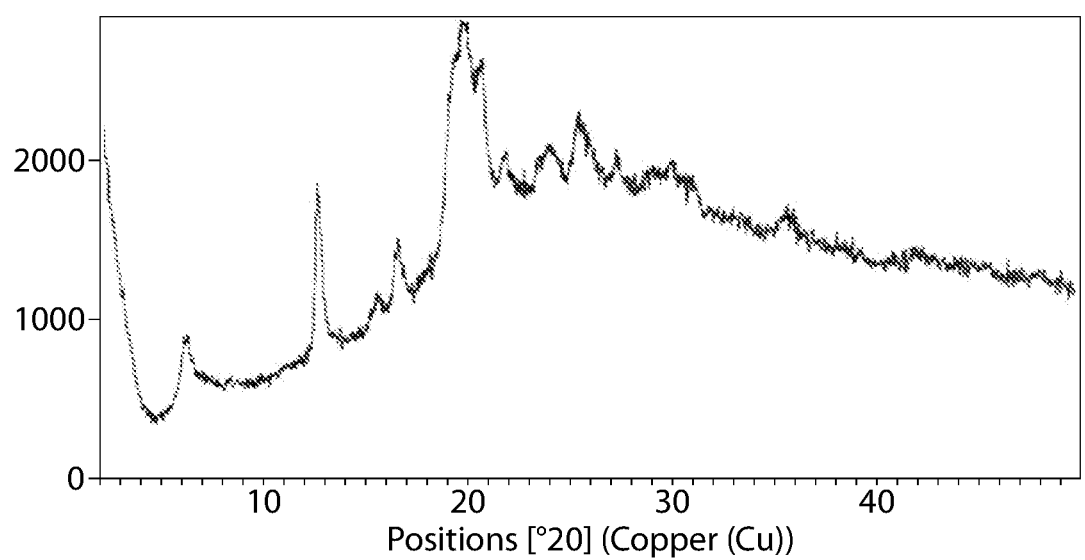
FIG. 4. is a X-ray Powder Diffraction of crystalline Lithium (2R,5S,13aR)-7,9-dioxo-10-((2,4,6-trifluorobenzyl) carbamoyl)-2,3,4,5,7,9,13,13a-octahydro-2,5-methanopyrido [1',2':4,5]pyrazino [2,1-b][1,3] oxazepin-8-olate compound of Formula-II.

Charged (2R,5S,13aR)-8-methoxy-7,9-dioxo-N-[(2,4,6-trifluorophenyl)methyl]-2,3,4,5,7,9,13,13a-octahydro-2,5-methanopyrido[1',2':4,5]pyrazino[2,1-b] [1,3] oxazepine-10-carboxamide (80 gm) in acetonitrile (960 ml) at 20-30° C. Lithium bromide (52.5 gm, 0.6045 moles) were added to the reaction mass in 4 lots for 30-40 minutes at 20-30° C. Heated the reaction mass to 60-65° C. and stirred for 3 hours. The reaction mass was Cooled to 20-30° C. and stirred for 3 hours. Filtered the obtained solid and washed with acetonitrile to yield the title compound and pxrd is same as depicted in FIG. 4.

Purity by HPLC (by chromatography): 98%.

Example-8: Preparation of (2R,5S,13aR)-7,9-dioxo-10-((2,4,6-trifluorobenzyl) carbamoyl)-2,3,4,5,7,9, 13,13a-octahydro-2,5-methanopyrido[1',2':4,5] pyrazino[2,1-b][1,3] oxazepin-8-olate (Compound of Formula-Ia)

Charged Lithium (2R,5S,13aR)-7,9-dioxo-10-((2,4,6-trifluorobenzyl) carbamoyl)-2,3,4,5,7,9,13,13a-octahydro-2,5-methanopyrido[1',2': 4,5]pyrazino[2,1-b][1,3] oxazepin-8-olate and Methanol (160 ml). Reaction mass pH was adjusted to 2.0 to 3.0 with Conc HCl at 20-30° C., stirred for 1 hour and concentrated. Concentrated mass was diluted with methanol (160 ml) and heated to 60-65° C., stirred for 1 hour, cooled to 0-5° C. and stirred for 4 hours to crystallize the product. The product was filtered, washed with chilled methanol and dried to yield the title compound.

Yield—78%; Purity by HPLC (by chromatography): 99.44%.

Example-9: Preparation of Sodium (2R,5S,13aR)-7, 9-dioxo-10-((2,4,6-trifluorobenzyl) carbamoyl)-2,3, 4,5,7,9,13,13a-octahydro-2,5-methanopyrido[1',2':4, 5]pyrazino[2,1-b] [1,3] oxazepin-8-olate (Compound of Formula-I)

Dissolving (2R,5S,13aR)-7,9-dioxo-10-((2,4,6-trifluorobenzyl) carbamoyl)-2,3,4,5,7,9,13, 13a-octahydro-2,5-methanopyrido[1',2': 4,5]pyrazino[2,1-b] [1,3] oxazepin-8-olate (50 g) in methylene dichloride at 25-30° C. Water was added to the above clear reaction mass and organic layer was separated. Organic layer was treated with carbon and passed through hyflow. Sodium hydroxide solution has been prepared by addition of ethanol (90 ml) and NaOH (4.9 gms) and stirred for 30 minutes. To the organic layer ethanolic sodium hydroxide solution was added for 45 minutes at 25-30° C. and stirred for 2 hrs to crystallize the product. The obtained product was filtered and dried to yield the title compound.

Yield—94%; Purity by HPLC (by chromatography): 99.60%.

We claim:
1. Crystalline Form HN-1 of Sodium (2R,5S,13aR)-7,9-dioxo-10-(2,4,6-trifluorobenzyl) carbamoyl)-2,3,4,5,7,9,13, 13a-octahydro-2,5-Methanopyrido [1',2':4,5]pyrazino[2,1-b][1,3]oxazepin-8-olate of compound of Formula-I

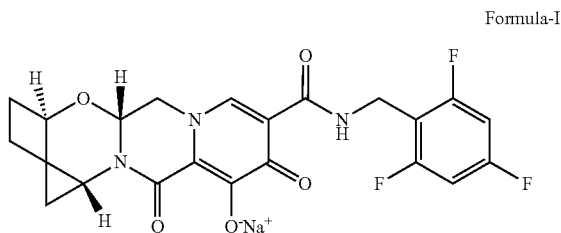

Formula-I characterized by an x-ray powder diffraction (XRPD) pattern comprising the peaks of 6.4, 9.0, 12.0, 15.9, 17.2 ,19.4, 20.9, 22.6, 23.2, and 25.7±0.2° 2θ.

2. The crystalline Form HN-1 of Sodium (2R,5S,13aR)-7,9-dioxo-10-((2,4,6-trifluorobenzyl) carbamoyl)-2,3,4,5,7, 9,13,13a-octahydro-2,5-Methanopyrido[1',2':4,5]pyrazino [2,1-b][1,3] oxazepin-8-olate of claim 1, is further characterized by an X-ray powder diffraction pattern as shown in FIG. 1.

3. The crystalline Form HN-1 of Sodium (2R,5S,13aR)-7, 9-dioxo-10-((2,4,6-trifluorobenzyl)carbamoyl)-2,3,4,5,7,9, 13,13a-octahydro-2,5-methanopyrido [1',2':4,5] pyrazino[2, 1-b][1,3] oxazepin-8-olate of claim 1 having water content in the range of 3-6% w/w by Karl Fischer method.

4. A process for the preparation of -Sodium (2R,5S, 13aR)-7, 9-dioxo-10-((2,4,6-trifluorobenzyl) carbamoyl)-2, 3,4,5,7,9,13,13a-octahydro-2, 5-Methanopyrido[1',2':4,5] pyrazino [2,1-b][1,3] Oxazepin-8-olate crystalline Form HN-1, which comprises:
 a) dissolving (2R,5S,13 aR)-7,9-dioxo-10-((2,4,6-trifluorobenzyl)carbamoyl)-2, 3,4,5,7,9,13,13a-octahydro-2, 5-Methanopyrido[1',2':4,5]pyrazino[2,1-b] [1,3] Oxazepin-8-olate, in an organic solvent, water and/or mixtures thereof;
 b) optionally treatment with carbon;
 c) preparing a source of sodium base;
 d) adding step-(c) to step-(a) or (b) or step-(a) or (b) to step-(c);
 e) heating the obtained reaction mixture to 40-50° C.;
 f) cooling the obtained reaction mixture to room temperature; and
 g) isolating Sodium (2R,5S,13aR)-7,9-dioxo-10-((2,4,6-trifluorobenzyl) carbamoyl)-2, 3,4,5,7,9,13,13a-octahydro-2,5-Methanopyrido[1',2':4,5] pyrazino [2,1-b][1, 3] oxazepin-8-olate in crystalline form.

5. The process according to claim 4, wherein the organic solvent is selected from the group consisting of halogenated solvents, alcohols, ketones, or mixtures thereof; wherein halogenated solvents are selected from dichloromethane (MDC), ethylene dichloride (EDC), and chloroform; alcohols are selected from methanol, isopropanol, n-propanol, and n-butanol; and ketonic solvents are selected from acetone and methylethyl ketone.

6. The process according to claim 4, wherein the sodium base is selected from the group consisting of sodium hydroxide, sodium alkoxide, sodium-2-ethylhexanoate, sodium acetate, sodium bicarbonate, sodium carbonate, sodium lactate, and sodium dihydrogen phosphate.

7. A method of treating Human Immunodeficiency Virus (HIV) by administering an effective amount of a pharmaceutical composition in need thereof comprising crystalline Form HN-1 of Sodium (2R,5S,13aR)-7,9-dioxo-10-((2,4,6-trifluorobenzyl)carbamoyl)-2,3,4,5,7,9,13,13a-octahydro-2,5-Methanopyrido [1',2':4,5]pyrazino[2,1-b][1,3] oxazepin-8-olate as claimed in claim 1 thereby treating Human Immunodeficiency Virus (HIV).

* * * * *